US011207253B2

(12) United States Patent
Sangirardi et al.

(10) Patent No.: US 11,207,253 B2
(45) Date of Patent: Dec. 28, 2021

(54) PRESERVATIVE COMPOSITIONS FOR FORMULATIONS

(71) Applicant: LONZA, LLC, Morristown, NJ (US)

(72) Inventors: Angela Marie Sangirardi, Saddle Brook, NJ (US); Susan Ahrendt Mills, Ringwood, NJ (US)

(73) Assignee: ARXADA, LLC, Morristown, NJ (US)

( * ) Notice: Subject to any disclaimer, the term of this patent is extended or adjusted under 35 U.S.C. 154(b) by 315 days.

(21) Appl. No.: 15/008,937

(22) Filed: Jan. 28, 2016

(65) Prior Publication Data

US 2016/0213585 A1 Jul. 28, 2016

Related U.S. Application Data

(60) Provisional application No. 62/108,756, filed on Jan. 28, 2015.

(51) Int. Cl.

| | | |
|---|---|---|
| *A61K 8/34* | (2006.01) | |
| *A61K 8/36* | (2006.01) | |
| *A01N 31/02* | (2006.01) | |
| *A01N 37/06* | (2006.01) | |
| *A61K 8/67* | (2006.01) | |
| *A61K 8/60* | (2006.01) | |
| *A61Q 17/00* | (2006.01) | |
| *A61Q 19/00* | (2006.01) | |
| *A61Q 5/02* | (2006.01) | |
| *A61Q 5/12* | (2006.01) | |
| *A61Q 5/10* | (2006.01) | |
| *A61Q 9/02* | (2006.01) | |
| *A61Q 13/00* | (2006.01) | |
| *A61Q 17/04* | (2006.01) | |
| *A61Q 19/04* | (2006.01) | |
| *A61Q 1/14* | (2006.01) | |
| *A61Q 1/02* | (2006.01) | |

(52) U.S. Cl.
CPC ............... *A61K 8/36* (2013.01); *A01N 31/02* (2013.01); *A01N 37/06* (2013.01); *A61K 8/34* (2013.01); *A61K 8/342* (2013.01); *A61K 8/345* (2013.01); *A61K 8/60* (2013.01); *A61K 8/678* (2013.01); *A61Q 17/005* (2013.01); *A61Q 19/00* (2013.01); *A61K 2800/10* (2013.01); *A61K 2800/524* (2013.01); *A61Q 1/02* (2013.01); *A61Q 1/14* (2013.01); *A61Q 5/02* (2013.01); *A61Q 5/10* (2013.01); *A61Q 5/12* (2013.01); *A61Q 9/02* (2013.01); *A61Q 13/00* (2013.01); *A61Q 17/04* (2013.01); *A61Q 19/002* (2013.01); *A61Q 19/004* (2013.01); *A61Q 19/04* (2013.01)

(58) Field of Classification Search
CPC .......... A61Q 5/12; A61Q 19/004; A61Q 1/00; A01N 31/02; A61K 2800/70
See application file for complete search history.

(56) References Cited

U.S. PATENT DOCUMENTS

| | | | |
|---|---|---|---|
| 5,539,001 A | 7/1996 | Waldmann-Laue et al. | |
| 7,537,776 B1 | 5/2009 | Beilfuss et al. | |
| 9,060,952 B2 | 6/2015 | Nunez et al. | |
| 2003/0147825 A1* | 8/2003 | Chiarelli | A61K 8/06 424/70.11 |
| 2009/0004122 A1* | 1/2009 | Modak | A61K 8/345 424/49 |
| 2009/0123577 A1* | 5/2009 | Beilfuss | A61K 8/34 424/729 |
| 2011/0086918 A1* | 4/2011 | Ciccognani | A61K 8/345 514/557 |
| 2011/0152383 A1 | 6/2011 | Schmaus et al. | |
| 2012/0201902 A1 | 8/2012 | Modak et al. | |
| 2015/0189872 A1 | 7/2015 | Gradtke et al. | |
| 2016/0128920 A1* | 5/2016 | Ranft | A61K 8/345 514/557 |

FOREIGN PATENT DOCUMENTS

| | | | | |
|---|---|---|---|---|
| WO | 2011/023582 A2 * | 3/2011 | ............. | A01N 31/02 |
| WO | WO 2013066403 A1 | 5/2013 | | |
| WO | WO2014009157 A1 * | 1/2014 | | |
| WO | 2014207179 * | 12/2014 | | |
| WO | WO 2014207179 A1 | 12/2014 | | |

OTHER PUBLICATIONS

Traul et al, title: Review of the toxicologic properties of medium-chain triglycerides; Food Chem Toxicol. Jan. 2000; 38(1):79-98.*
Bergfeld et al., title: safety assessment of tocopherol and tocotrienols as used in cosmetics, release date Dec. 18, 2013. downloaded from https://www.cir-safety.org/sites/default/files/tocoph122013TAR.pdf on Feb. 7, 2018.* Cremer Oleo GmbH & Co. KG ("Cremer", Cremer Care inspired by nature, Title: MIGLYOL® 810, 812, INCI: Caprylic/Capric Triglyceride; published Mar. 2013. (Year: 2013).*
Unknown author, title: MIGLYOL® 810, 812, published by Cremer Care on Mar. 2013. (Year: 213).*
PCT/US2016/015315 International Search Report and Written Opinion dated Mar. 22, 2016, 13 pages.
Database Caplus (Online), Chemical Abstracts Service, Columbus, Ohio, US; Weber, K. et al.: Organic acids—a fashionable alternative for cosmetics,, XP002529502, retrieved from STN database accession No. 2003:744006 abstract.

(Continued)

*Primary Examiner* — Yanzhi Zhang

(74) *Attorney, Agent, or Firm* — Dority & Manning, P.A.

(57) ABSTRACT

A preservative composition is described that may be used in personal care products and other products for protecting the products against bacteria and fungus during production and during use. The composition can about 3 to about 15% by weight of an organic acid; about 3 to about 15% by weight of a $C_8$-$C_{18}$ fatty alcohol; about 30 to about 60% by weight of an aromatic alcohol; and about 30 to about 60% by weight of an organic solvent.

22 Claims, No Drawings

(56) References Cited

OTHER PUBLICATIONS

Anonymous: Mikrokill TM Ect, Internet Citation, Jan. 29, 2010, pp. 1-8, XP002712123, Retrieved from the Internet: URL: http://az290931.082290231. Vo.msecnd. Net/www.in-cosmetics.com/_novadocuments/2198x$query$xvx$eq$x634484823552730000 [retrieved on Sep. 11, 2013] Figure 1, p. 5, table 1.

* cited by examiner ated compositions can be added to form a preservative composition of the present invention. In particular, the compositions can be added to a base formulation which could be, for example, a shampoo, a hair conditioner, a hair dye, an aftershave, a shave preparation, a bath soap, a perfume, a sun care product, an indoor tanning product, a body or hand lotion, a personal cleaner, a skin care product, a baby care product, a make-up remover, make-up or a wet wipe formulation.

PRESERVATIVE COMPOSITIONS FOR FORMULATIONS

RELATED APPLICATIONS

The present application is based on and claims priority to U.S. Provisional Patent application Ser. No. 62/108,756, which was filed on Jan. 28, 2015, and which is incorporated herein by reference.

FIELD OF INVENTION

The present invention relates to a preservative composition for use in a variety of formulations to preserve the formulation both prior to and during use.

BACKGROUND OF THE INVENTION

Preservative compositions for protecting and preserving formulations against bacterial or fungal attack are known in the art. These preservative compositions have a wide variety of applications in fields such as personal care products, household and industrial products, health and hygiene products, and pharmaceuticals. Conventional preservative blends have used traditional active ingredients such as formaldehyde releasers and/or parabens due to the good bacterial and fungicidal properties achieved by these types of compounds.

There is a trend in the personal care industry for new and alternative preservative compositions. To answer that need, combinations of compounds have been suggested to achieve a final use formulation which is resistant to both bacteria and fungus. An example of such is disclosed in US Patent Application Publication US2011/0301206 A1 to Nunez et al, which teaches a blend of both lauryl alcohol and sorbic acid, among other combinations, as a preservative combination added to a formulation to be protected from bacteria and/or fungus. Other preservative compositions are disclosed in US Patent Application Publication US2011/0086918 A1 to Ciccognani et al., which teaches a blend of benzyl alcohol, salicylic acid, sorbic acid, and at least one of 1,3-propanediol, glycerin or a combination of 1,3-propanediol and glycerin as a composition which can be added to use formulation to preserve the use formulation against bacteria and fungus.

The above are effective as preservatives in the use formulation; however, there is a need in the art for faster-acting preservative compositions and preservative compositions which are easy to add or formulate into end use formulations that need preservation. Further, there is a desire in the industry to have preservatives which are from naturally occurring or contain ECOCERT certified components to be used in cosmetics, shampoos, lotions and other similar personal care products. The present invention provides an answer to that need.

SUMMARY OF THE INVENTION

In one embodiment of the present invention, provided is a fluid preservative composition containing
(i) about 3 to about 15% by weight of an organic acid;
(ii) about 3 to about 15% by weight of a $C_8$-$C_{18}$ fatty alcohol;
(iii) about 30 to about 60% by weight of an aromatic alcohol; and
(iv) about 30 to about 60% by weight of an organic solvent.

The preservative composition provides protection of a base formulation against bacteria and fungus infection or contamination.

In a second embodiment the preservative composition contains sorbic acid as the organic acid.

In a further embodiment, the solvent is a diol compound. Diol compounds include, for example propanediol, butanediol, pentanediol, hexanediol, heptanediol, and a mixture of two or more of the diols. In a particular embodiment, the diol solvent is 1,3-butanediol.

In another embodiment of the present invention, the aromatic alcohol includes benzyl alcohol.

In yet another embodiment of the present invention, the $C_8$-$C_{18}$ fatty alcohol is lauryl alcohol, myristyl alcohol or a mixture of lauryl alcohol and myristyl alcohol.

In yet another embodiment, the preservative composition comprising a stabilizer in an amount up to 5% by weight, such as in an amount of from about 0.1% to about 1% by weight. Suitable stabilizers include tocopherol and gluconolactone.

In a further embodiment of the present invention, the preservative composition further contains a dispersant or solubilizer in an amount from about 1% up to about 20%. In one embodiment the solubilizer comprises at least one triglyceride, such as caprylic/capric triglycerides.

In further embodiments, the preservative composition comprises from about 4% to about 10%, such as from about 4% to about 9% by weight of the organic acid, from about 4% to about 10%, such as from about 4% to about 9% by weight of the $C_8$-$C_{18}$ fatty alcohol, from about 35% to about 45% by weight, such as from about 37.5% to about 42.5% by weight of the aromatic alcohol, and from about 35% to about 50% by weight, such as from about 40% to about 45% by weight of the organic solvent.

In one particular embodiment, the organic acid is sorbic acid, the fatty alcohol comprises a mixture of lauryl alcohol and myristyl alcohol, the aromatic alcohol comprises benzyl alcohol and the organic solvent comprises 1,3-butanediol.

In a different embodiment, provided is a personal care product containing a base formulation and an effective amount of the preservative composition of any one of the previous embodiments to aid in preventing a bacterial and/or fungal infection or contamination of the base formulation. The personal care product contains between about 0.1% to about 5% by weight of the preservative composition.

In another embodiment of the personal care product aspect of the present invention, the base formulation is a formulation, for example, a shampoo, a hair conditioner, a hair dye, an aftershave, a shave preparation, a bath soap, a perfume, a sun care product, an indoor tanning product, a body or hand lotion, a personal cleaner, a skin care product, a baby care product, a make-up remover, make-up or a wet wipe formulation.

In yet a different embodiment of the present invention provides a method of preserving a personal care formulation in need of preservation against bacteria and fungus infection or contamination. The method includes adding the preservative composition in any of the embodiments of the present invention to a base formulation, and mixing the preservative composition with the base formulation.

These and other aspects will become apparent when reading the detailed description of the invention.

DETAILED DESCRIPTION OF EMBODIMENTS

It has now been surprisingly found that the preservative composition of the present invention is an effective preservative composition that can be used to preserve a wide variety of formulations, in particular personal care formulations.

The composition of the present disclosure can provide numerous benefits and advantages. As indicated above, the composition may provide a personal care product with antimicrobial stability. Of particular advantage, the composition can be formulated so as to be made exclusively or mostly from all natural ingredients or ingredients which are ECOCERT certified. In this regard, the composition can replace more traditional preservative systems. When functioning as a preservative, the composition has displayed a wide variety of antimicrobial activity against numerous bacteria and fungi.

As used herein, the term "composition" refers to the preservative composition of the present invention.

As used herein, the term "formulation" is intended to refer to preparations that have a specific utility that are to be preserved with the composition of the present invention.

The preservative composition of the present invention is a composition which contains (i) an organic acid; (ii) a $C_8$-$C_{18}$ fatty alcohol; (iii) an aromatic alcohol and (iv) an organic solvent. The amounts of each ingredient of the preservative composition may vary, provided that each of the ingredients is with the following ranges:

(i) about 3 to about 15% by weight of organic acid;

(ii) about 3 to about 15% by weight of a $C_8$-$C_{18}$ fatty alcohol;

(iii) about 30 to about 60% by weight of an aromatic alcohol; and (iv) about 30 to about 60% by weigh of an organic solvent The organic acids useable in the present invention are those organic acids which have antimicrobial properties. Usable acids include acids such as sorbic acid (hexadienoic acid), benzoic acid, dehydroacetic acid, formic acid, acetic acid, propionic acid, undecenoic acid, salicylic acid and glycolic acid. Of these acids, sorbic acid is of particular interest due to its activity and other properties, including being naturally occurring. Generally, the organic acid is present in an amount between about 3% and about 15% by weight of the preservative composition, more typically between about 4% and about 10% by weight of the composition, and more typically in an amount between about 4% and about 9% by weight of the preservative composition.

The fatty alcohol usable in the present invention includes fatty alcohols having 8 to 18 carbon atoms. Exemplary fatty alcohols included capryl alcohol, nanoyl alcohol, decyl alcohol, undecyl alcohol, lauryl alcohol, tridecyl alcohol, myristyl alcohol, pentadecyl alcohol, palmityl alcohol, margaryl alcohol and stearyl alcohol. Of these alcohols, the ones with an even number of carbon atoms are preferred. Of particular interest is lauryl alcohol and myristyl alcohol. One particular alcohol is naturally occurring lauryl alcohol which is a blend of $C_8$ to $C_{18}$ alcohols, but is predominately a mixture of lauryl alcohol and myristyl alcohol. An exemplary fatty alcohol which is a mixture of lauryl alcohol and myristyl alcohol is commercially available and can be ECOCERT compliant. Generally, the fatty alcohol is present in an amount between about 3% and about 15% by weight of the preservative composition, more typically between about 4% and about 10% by weight of the composition, and more typically in an amount between about 4% and about 9% by weight of the preservative composition.

Suitable aromatic alcohols useable in the preservative composition of the present invention includes, for example, benzyl alcohol, phenoxyethanol, phenethyl alcohol and other similar aromatic alcohols. Of these aromatic alcohols, benzyl alcohol is preferred since it meets ECOCERT criteria. Generally, the aromatic alcohol is present in an amount between about 30% and about 60% by weight of the preservative composition, more typically between about 35% and about 45% by weight of the composition, and more typically in an amount between about 37.5% and about 42.5% by weight of the preservative composition.

The organic solvent may comprise a diol. For instance, the solvent may comprise propanediol, butanediol, pentanediol, hexanediol, or heptanediol. In one particular embodiment, the solvent comprises 1,5-pentanediol, 1,4-butanediol, 1,3-butanediol, or mixtures thereof. Of particular interest as a solvent is 1,3-butanediol, some of which are ECOCERT. Generally, the solvent is present in an amount between about 30% and about 60% by weight of the preservative composition, more typically between about 35% and about 50% by weight of the composition, and more typically in an amount between about 40% and about 45% by weight of the preservative composition.

Optionally, the preservative composition may also contain additional ingredients such as a dispersant, a solubilizer or a stabilizer. A dispersant may be used in order to help stabilize the preservative composition and some dispersants may also function as a solubilizer. A solubilizer may be used to solubilize the components of the preservative composition into the solvent. A stabilizer or antioxidant is a component that prevents one or more of the active ingredients from losing its activity or decaying in the preservative composition.

Various dispersants may be used in accordance with the present disclosure. As with the other ingredients, preferred dispersants comprise natural ingredients. In one embodiment, for instance, the dispersant may comprise a polyglycerol ester, also known as a polyglycerides. In addition, polyglycerides or various other non-ionic surfactants may also be used as the dispersant, particularly if the material can be obtained from natural sources.

In one embodiment, the dispersant comprises a polyglycerol ester of a fatty acid. In general, the polyglycerol ester can contain an average of from about two glycerol groups per molecule to about 15 glycerol groups per molecule, such as from about three glycerol groups per molecule to about 6 glycerol groups per molecule.

The fatty acid that is combined with the polyglycerol may comprise any suitable fatty acid that has a chain length of from about one carbon atom to about 28 carbon atoms, such as from about three carbon atoms to about 24 carbon atoms. In fact, any of the organic fatty acids described above may be used to produce the polyglycerol ester. Examples of polyglycerol esters that may be used as a dispersant include polyglycerol-10 oleate, polyglycerol-10 caprylate, polyglycerol-10 caprate, and mixtures thereof.

Suitable solubilizers included components such as mineral oil, and glycerin compounds. One particular solubilizer, which may also function as a dispersant for some components in the preservative composition. Glycerin compounds, such as a caprylic/capric triglyceride, which is believed to be a mixed triester of glycerin and caprylic and capric acids, is of particular interest since it is vegetable-based and is non-GMO (genetically modified organism).

When present in the composition, the dispersant or solubilizer may be included in an amount from about 1% to about 20% by weight, such as in an amount from about 4% to about 8% by weight of the composition.

Stabilizers which may be used in the present invention include compounds such as tocopherol and gluconolactone or other similar compounds. Stabilizers may be present in an amount up to about 5% by weight. Generally, the stabilizers are present in an amount of about 0.1 to about 2% by weight. The stabilizer helps maintain the acid groups on the organic acid compound so that the acid group remains functional in the preservative composition of the present invention over an extended period of time.

The preservative composition of the present invention is typically water-free, but may contain trace amounts of water. By having a water-free preservative composition, the preservative composition will have better stability and be storage stable at low temperatures that the composition may be exposed to during shipment. In addition, the active ingredients are not typically highly-soluble in water.

The preservative composition may be incorporated into a wide variety of formulations as a method of reducing incidental bacterial and fungal load in the formulation. The method generally includes adding preservative compositions to the formulation to be preserved. The preferred bactericidal and fungicidal compounds, their preferred concentrations and combinations are as stated above.

In general, the preservative composition of the present invention can be incorporated into any suitable personal care product. For instance, the personal care product may comprise a cosmetic formulation, such as a face cream, makeup remover, mascara or wet wipe. The personal care product formulation may also comprise shampoo, a conditioner, skin lotion or liquid for any personal care wet wipe application. The personal care product formulation may comprise any product for topical application to a user's skin or hair. When combined with the personal care product formulation as a preservative, the composition has effective broad spectrum preservation activity over a broad pH range. For instance, the pH of the composition and/or of the personal care product can be generally greater than about 2 and less than about 9, such as from about 3 to about 8, particularly from about 3 to about 6.

The personal care product formulation generally comprises a base formulation to which the preservative composition of the present disclosure is added. The base formulation may contain numerous and different ingredients depending upon the end use application. The personal care product formulation, for instance, may contain solvents, surfactants, emulsifiers, consistency factors, conditioners, emollients, skin caring ingredients, moisturizers, thickeners, lubricants, fillers, anti-oxidants, other preservatives, active ingredients, in particular dermatologically active ingredients, fragrances and the like, as well as mixtures thereof. Active ingredients as mentioned herein comprise, for example, anti-inflammatories, anti-bacterials, anti-fungals and the like agents. Active ingredients suited for topical applications are particularly preferred.

Suitable surfactants comprise: alkyl sulfates e.g. sodium lauryl sulfate, ammonium lauryl sulfate; sodium cetearyl sulfate; alkyl sulfoacetates e.g. sodium lauryl sulfoacetate; alkyl ether sulfates e.g. sodium laureth sulfate; sodium trideceth sulfate; sodium oleth sulfate; ammonium laureth sulfate; alkyl ether sulfosuccinates e.g. disodium laureth sulfosuccinate; alkyl glycosides e.g. decyl glucoside; lauryl glucoside; alkyl isethionates amphoterics e.g. cocamidopropyl betaine; sodium cocoamphoacetate; sodium lauroamphoacetate; disodium lauroamphodiacetate; disodium cocoamphodiacetate; sodium lauroamphopripionate; disodium lauroamphodipropionate; potassium or ammonium salts of the aforementioned amphoterics; capryl/capramidopropyl betaine; undecylenamidopropyl betaine; lauromidopropyl betaine; and fatty alcohol polyglycol ethers.

Suitable emulsifiers are e.g. anionics as salts of fatty acids e.g. sodium stearate or sodium palmitate, organic soaps e.g. mono-, di- or triethanolaminoeate, sulfated or sulfonated compounds e.g. sodium lauryl sulfate or sodium cetyl sulfonate, saponines, lamepones; cationics as quaternary ammonium salts; nonionics as fatty alcohols, fatty acid ester with saturated or unsaturated fatty acids, polyoxyethylenesters or polyoxyethylenethers of fatty acids, polymers from ethylene oxide and propylene oxide or propylene glycol, amphotherics as phosphatides, proteins as gelatine, casein alkylamidobetaines, alkyl betaines and amphoglycinates, alkyl phosphates, alkylpolyoxyethylene phosphates or the corresponding acids, silicone derivatives, e.g. alkyl dimethiconecoplyol.

Suitable consistency factors are e.g. fatty alcohols or their mixtures with fatty acid esters, e.g. acetylated lanolin alcohol, aluminum stearates, carbomer, cetyl alcohol, glyceryl oleate, glyceryl stearate, glyceryl stearate (and) PEG 100 stearate, magnesium stearate, magnesium sulfate, oleic acid, stearic acid, stearyl alcohol, myristyl myristate, isopropyl palmitate, beeswax and synthetic equivalents thereof, carbomers, and the like. Suitable conditioners are e.g. alkylamido ammonium lactate, cetrimonium chloride and distearoylethyl hydroxyethylmonium methosulfate and cetearyl alcohol, cetyl dimethicone, cetyl ricinoleate, dimethicone, laureth-23, laureth-4, polydecene, retinyl palmitate, quaternized protein hydrolysates, quaternized cellulose and starch derivatives, quaternized copolymers of acrylic or methacrylic acid or salts, quaternized silicone derivatives.

Suitable emollients are e.g. cetearyl isononanoate, cetearyl octanoate, decyl oleate, isooctyl stearate, coco caprylate/caprate, ethylhexyl hydroxystearate, ethylhexyl isononanoate, isopropyl isostearate, isopropyl myristate, oleyl oleate, hexyl laurate, paraffinum liquidum, PEG-75 lanolin, PEG-7 glyceryl cocoate, petrolatum, ozokerite cyclomethicone, dimethicone, dimethicone copolyol, dicaprylyl ether, butyrospermum parkii, buxus chinensis, canola, carnauba cera, copernicia cerifera, *Oenothera biennis, Elaeis guineensis*, prunus dulcis, squalane, *Zea mays*, glycine soja, *Helianthus annuus*, lanolin, hydrogenated castor oil, hydrogenated coconut oil, hydrogenated polyisobutene, sucrose cocoate, stearoxy dimethicone, lanolin alcohol, isohexadecane.

Suitable skin care ingredients are e.g. plant extracts, bisabolol, anti-inflammatory agents, urea, allantoin, panthenol and panthenol derivatives, phytantriol, vitamins A, E, C, D, ceram ides of animal or plant origin, lecithins, and the like.

Suitable moisturizers are e.g. butylenes glycol, cetyl alcohol, dimethicone, dimyristyl tartrate, glucose glycereth-26, glycerin, glyceryl stearate, hydrolyzed milk protein, lactic acid, lactose and other sugars, laureth-8, lecithin, octoxyglycerin, PEG-12, PEG 135, PEG-150, PEG-20, PEG-8, pentylene glycol, hexylene glycol, phytantriol, poly quaternium-39 PPG-20 methyl glucose ether, propylene glycol, sodium hyaluronate, sodium lactate, sodium PCA, sorbitol, succinoglycan, synthetic beeswax, tri-C14-15 alkyl citrate, starch.

Suitable thickeners are e.g. acrylates/steareth-20 methacrylate copolymer, carbomer, carboxymethyl starch, cera alba, dimethicone/vinyl dimethicone crosspolymer, propylene glycol alginate, hydroxyethylcellulose, hydroxypropyl methylcellulose, silica, silica dimethyl silylate, xanthan gum, hydrogenated butylenes/ethylene/styrene copolymer.

Suitable lubricants are e.g. adipic acid, fumaric acid and its salts, benzoic acid and its salts, glycerine triacetate, sodium or magnesium lauryl sulfate, magnesium stearate, solid polyethylenglycol, polyvinylpyrrolidone, boric acid, mono-laurate or mono-palmitate, myristyl alcohol, cetyl alcohol, cetylstearyl alcohol, talcum, calcium or magnesium salts of higher fatty acids, mono-, di- or triglycerides of higher fatty acids, polytetrafluorethylene.

Suitable antioxidants are e.g. sulfites, e.g. sodium sulfite, tocopherol or derivates thereof, ascorbic acid or derivates thereof, citric acid, propyl gallate, chitosan glycolate, cysteine, N-acetyl cysteine plus zinc sulfate, thiosulfates, e.g. sodium thiosulfate, polyphenols and the like.

The formulations may further contain active ingredients, e.g. antimicrobials, anti-inflammatories, plant extracts, bisabolol, panthenol, tocopherol, actives for anti-stinging, anti-irritant or anti-dandruff applications, or anti-aging agents such as retinol, melibiose and the like. Other suitable actives are e.g. *Medicago officinalis, Actinidia chinensis*, allantoin, *Aloe barbadensis, Anona cherimolia, Anthemis nobilis, Arachis hypogaea, Arnica Montana, Avena sativa*, beta-carotene, bisabolol, *Borago officinalis*, butylenes glycol, *Calendula officinalis, Camellia sinensis*, camphor, *Candida bombicola*, capryloyl glycine, *Carica papaya, Centaurea cyanus*, cetylpyridinium chloride, *Chamomilla recutita, Chenopodium quinoa, Chinchona succirubra, Chondrus crispus, Citrus aurantium dulcis, Citrus grandis, Citrus limonum, Cocos nucifera, Coffea Arabica, Crataegus monogina, Cucumis melo*, dichlorophenyl imidazoldioxolan, *Enteromorpha compressa, Equisetum arvense*, ethoxydiglycol, ethyl panthenol, farnesol, ferulic acid, *Fragaria chiloensis, Gentiana lutea, Ginkgo biloba*, glycerin, glyceryl laurate, *Glycyrrhiza glabra, Hamamelis virginiana*, heliotropine, hydrogenated palm glycerides, citrates, hydrolyzed castor oil, hydrolyzed wheat protein, *Hypericum perforatum, Iris florentina, Juniperus communis, Lactis proteinum*, lactose, *Lawsonia inermis*, linalool, *Linum usitatissimum*, lysine, magnesium aspartate, *Magnifera indica, Malva sylvestris*, mannitol, mel *Melaleuca alternifolia, Mentha piperita*, menthol, menthyl lactate, *Mimosa tenuiflora, Nymphaea alba*, olaflur, *Oryza sativa*, panthenol, paraffinum liquidum, PEG-20M, PEG-26 jojoba acid, PEG-26 jojoba alcohol, PEG-35 castor oil, PEG-40 hydrogenated castor oil, PEG-60 hydrogenated castor oil, PEG-8 caprylic/capric acid, *Persea gratissima*, petrolatum, potassium aspartate, potassium sorbate, propylene glycol, *Prunus amygdalus dulcis, Prunus armeniaca, Prunus persica*, retinyl palmitate, *Ricinus communis, Rosa canina, Rosmarinus officinalis, Rubus idaeus*, salicylic acid, *Sambucus nigra*, sarcosine, *Serenoa serrulata, Simmondsia chinensis*, sodium carboxymethyl betaglucan, sodium cocoyl amino acids, sodium hyaluronate, sodium palmitoyl praline, stearoxytrimethylsilane, stearyl alcohol, sulfurized TEA-ricinoleate, talc, *Thymus vulgaris, Tilia cordata*, tocopherol, tocopheryl acetate, trideceth-9, *Triticum vulgare*, tyrosine, undecylenoyl glycine, urea, *Vaccinium myrtillus*, valine, zinc oxide, zinc sulfate.

The preservative composition of the present disclosure can be used in emulsions (both oil-in-water and water-in-oil), in aqueous solutions, in PIT (phase inversion temperature) emulsions, in oily solutions, in foaming cosmetic formulations (foams), and in so-called multiple emulsions, e.g. in triple emulsions (such as water/oil/water emulsions).

The preservative composition of the present disclosure can also be formulated as creams, gels, liquids or lotions. They can be used in hair care products such as shampoos, hair conditioners, hair dyes, hair tonic, hair gel, hair dressings, hair grooming aids and other hair care preparations; shaving applications such as shaving cream, aftershave lotions, and other shaving applications; personal cleaners for the body and hands, such as liquid bath soaps and detergents; fragrance preparations, such as perfumes, after bath splashes, and other similar fragrant preparations, skin care products, such as moisturizers, creams, and lotions and other similar skin care products, make-up products, such as mascara, base foundations and the like; make-up removal products, sun care products, indoor tanning products and other similar personal care products. One particular use of the present preservative formulation is as a preservative for the composition used to saturate wipes, used for personal cleaning and hygiene (for example baby wipes, wet toilet wipes, make-up removal wipes and exfoliating wipes the like. The preservative composition may also be used in other formulations that are currently used in non-personal care products such as industrial products, hard surface hygiene products, health products, and the like.

Typically, the preservative composition of the present invention is added to a formulation to be preserved in an amount between 0.1% to about 5% by weight of the formulation. More particularly, the preservative composition is added in an amount which is between about 1.5 and 3.0% by weight of the formulation.

The present invention is further described in detail by means of the following Examples. All parts and percentages are by weight and all temperatures are degrees Celsius unless explicitly stated otherwise.

EXAMPLES

Example 1

A preservative composition is prepared by mixing benzyl alcohol with 1,3 butanediol to form a solution in the proportions shown in Table 1. This solution is heated to about 40° C. and lauryl-myristyl alcohol, sorbic acid, caprylic/capric triglyceride, and 0.5 parts by weight of tocopherol are added sequentially. The mixture is allowed to cool to room temperature prior to use. Each Sample is made the same way and the percentage by weight of each component is shown in Table 1.

TABLE 1

Preservative Composition

| Sample # | Sorbic acid | Lauryl/myristyl alcohol | Benzyl alcohol | 1,3-butanediol | Caprylic/capric trigylceride | Tocopherol |
|---|---|---|---|---|---|---|
| 1 | 6% | 6% | 45% | 37.5% | 5% | 0.5% |
| 2 | 5% | 6% | 40% | 43.5% | 5% | 0.5% |
| 3 | 4% | 6% | 42% | 41.5% | 6% | 0.5% |
| 4 | 6% | 4% | 42% | 41.5% | 6% | 0.5% |
| 5 | 6% | 5% | 40% | 43.5% | 5% | 0.5% |
| 6 | 6% | 6% | 35% | 47.5% | 5% | 0.5% |

All are % by weight

Example 2

CTFA challenge testing was carried out to show that the preservative composition of the present disclosure as described in Table 1 may be used to protect personal care formulations from microbial contamination. The CTFA cosmetic challenge protocol was followed using five separate inocula:

| | |
|---|---|
| Pool 1 | *Staphylococcus aureus* (ATCC 6538), |
| Pool 2 | *Pseudomonas aeruginosa* (ATCC 9027) + *Burkholderia cepacia* (ATCC 25416), |
| Pool 3 | *Klebsiella pneumoniae* (ATCC 4352) + *Enterobacter gergoviae* (ATCC 33028), |
| Pool 4 | *Candida albicans* (ATCC 10231), |
| Pool 5 | *Aspergillus brasiliensis* (ATCC 16404) + *Penicillium purpurogenum* (DSM 62 86) |

The inocula contain approximately 1,000,000 bacteria per gram or 100,000 yeast cells or mold spores per gram. Individual challenges were prepared from overnight slants of bacteria and yeast cultures and from heavily sporulating mold cultures, 7 to 10 days old. Test samples were made by adding each of the 2% of the samples #1-6 to a test lotion base which is an emulsion as is set forth in TEST SAMPLES A-F. All samples were plated (Bacteria in Tryptic Soy agar and Fungi in Malt Agar) quantitatively for viable organisms after 48 hours and weekly for 4 weeks. Modified Letheen Broth with 0.5% Tween 80 and 0.07% Lecithin added was used as a neutralizer. Samples inoculated with mold spores were also plated after 48 hours. Four weeks after the initial challenge, samples were challenged again and the same sampling regime followed. In addition, the tests were also conducted on unpreserved lotion base for purposes of comparison.

Test Sample A

A lotion base having pH of 6.0 having a 2% add-on of the Sample #1 was formed. The result for each of the organism inoculated into the test sample is reported in TABLE 2 for the first inoculation and TABLE 3 for the second inoculation performed after 4 weeks.

TABLE 2

(first inoculation)

| | Contact time | 0 h | 24 h | 48 h | 1 week | 2 weeks | 3 weeks | 4 weeks |
|---|---|---|---|---|---|---|---|---|
| Bacteria | S1 *Staphylococcus aureus* | $10^6$ | 130 | <10 | <10 | <10 | <10 | <10 |
| | S2 *Pseudomonas aeruginosa, Burkholderia cepacia* | $10^6$ | 330 | <10 | <10 | <10 | <10 | <10 |
| | S3 *Klebsiella pneumoniae, Enterobacter gergoviae* | $10^6$ | <10 | 10 | <10 | <10 | <10 | <10 |
| Fungi | S4 *Candida albicans* | $10^5$ | $1.5 \times 10^3$ | 40 | <10 | <10 | <10 | <10 |
| | S5 Mixed Moulds | $10^5$ | $10^4$ | 500 | <10 | <10 | <10 | <10 |

TABLE 3

(second inoculation)

| | Contact time | 0 h | 24 h | 48 h | 1 week | 2 weeks | 3 weeks | 4 weeks |
|---|---|---|---|---|---|---|---|---|
| Bacteria | S1 *Staphylococcus aureus* | $10^6$ | 40 | <10 | <10 | <10 | <10 | <10 |
| | S2 *Pseudomonas aeruginosa, Burkholderia cepacia* | $10^6$ | <10 | <10 | 10 | <10 | <10 | <10 |
| | S3 *Klebsiella pneumoniae, Enterobacter gergoviae* | $10^6$ | <10 | <10 | <10 | <10 | <10 | <10 |
| Fungi | S4 *Candida albicans* | $10^5$ | $2.7 \times 10^3$ | 60 | <10 | <10 | <10 | <10 |
| | S5 Mixed Moulds | $10^5$ | $10^4$ | $10^4$ | <10 | <10 | <10 | <10 |

As can be seen from the above Table 2 and Table 3, the preservative composition is effective in preserving the lotion, achieving the desired result of less than 10 cfu/gram 1 week after the first and second inoculations.

Test Sample B

A lotion base having pH of 6 having a 2% add-on of the Sample #2 was formed. The result for each of the organism inoculated into the test sample is reported in TABLE 4 for the first inoculation and TABLE 5 for the second inoculation performed after 4 weeks.

TABLE 4

| | | (first inoculation) | | | | | | |
|---|---|---|---|---|---|---|---|---|
| | Contact time | 0 h | 24 h | 48 h | 1 week | 2 weeks | 3 weeks | 4 weeks |
| Bacteria | S1 Staphylococcus aureus | $10^6$ | $4 \times 10^3$ | 10 | 10 | <10 | <10 | <10 |
| | S2 Pseudomonas aeruginosa, Burkholderia cepacia | $10^6$ | <10 | <10 | <10 | <10 | <10 | <10 |
| | S3 Klebsiella pneumoniae, Enterobacter gergoviae | $10^6$ | 10 | <10 | <10 | <10 | <10 | <10 |
| Fungi | S4 Candida albicans | $10^5$ | $6.3 \times 10^2$ | 50 | 20 | <10 | <10 | <10 |
| | S5 Mixed Moulds | $10^5$ | $10^4$ | $2 \times 10^2$ | <10 | <10 | <10 | <10 |

TABLE 5

| | | (second inoculation) | | | | | | |
|---|---|---|---|---|---|---|---|---|
| | Contact time | 0 h | 24 h | 48 h | 1 week | 2 weeks | 3 weeks | 4 weeks |
| Bacteria | S1 Staphylococcus aureus | $10^6$ | $3.5 \times 10^2$ | 40 | <10 | <10 | <10 | <10 |
| | S2 Pseudomonas aeruginosa, Burkholderia cepacia | $10^6$ | <10 | <10 | <10 | <10 | <10 | <10 |
| | S3 Klebsiella pneumoniae, Enterobacter gergoviae | $10^6$ | <10 | <10 | <10 | <10 | <10 | <10 |
| Fungi | S4 Candida albicans | $10^5$ | $2.6 \times 10^2$ | <10 | <10 | <10 | <10 | <10 |
| | S5 Mixed Moulds | $10^5$ | $7.5 \times 10^2$ | $6 \times 10^2$ | <10 | <10 | <10 | <10 |

Test Sample C

A lotion base having pH of 5 having a 2% add-on of the Sample #3 was formed. The results for each of the organisms inoculated into the test sample is reported in TABLE 6 for the first inoculation and TABLE 7 for the second inoculation performed after 4 weeks.

TABLE 6

| | | (first inoculation) | | | | | | |
|---|---|---|---|---|---|---|---|---|
| | Contact time | 0 h | 24 h | 48 h | 1 week | 2 weeks | 3 weeks | 4 weeks |
| Bacteria | S1 Staphylococcus aureus | $10^6$ | <10 | <10 | <10 | <10 | <10 | <10 |

TABLE 6-continued (first inoculation)

|  | Contact time | 0 h | 24 h | 48 h | 1 week | 2 weeks | 3 weeks | 4 weeks |
|---|---|---|---|---|---|---|---|---|
|  | S2 Pseudomonas aeruginosa, Burkholderia cepacia | $10^6$ | <10 | <10 | <10 | <10 | <10 | <10 |
|  | S3 Klebsiella pneumoniae, Enterobacter gergoviae | $10^6$ | <10 | <10 | <10 | <10 | <10 | <10 |
| Fungi | S4 Candida albicans | $10^5$ | $1.6 \times 10^2$ | <10 | <10 | <10 | <10 | <10 |
|  | S5 Mixed Moulds | $10^5$ | $5.3 \times 10^2$ | 50 | <10 | <10 | <10 | <10 |

TABLE 7

(second inoculation)

|  | Contact time | 0 h | 24 h | 48 h | 1 week | 2 weeks | 3 weeks | 4 weeks |
|---|---|---|---|---|---|---|---|---|
| Bacteria | S1 Staphylococcus aureus | $10^6$ | <10 | <10 | <10 | <10 | <10 | <10 |
|  | S2 Pseudomonas aeruginosa, Burkholderia cepacia | $10^6$ | <10 | <10 | <10 | <10 | <10 | <10 |
|  | S3 Klebsiella pneumoniae, Enterobacter gergoviae | $10^6$ | <10 | <10 | <10 | <10 | <10 | <10 |
| Fungi | S4 Candida albicans | $10^5$ | 60 | <10 | <10 | <10 | <10 | <10 |
|  | S5 Mixed Moulds | $10^5$ | $10^3$ | $2.4 \times 10^2$ | <10 | <10 | <10 | <10 |

Test Sample D

A lotion base having pH of 6 having a 2% add-on of the Sample #4 was formed. The results for each of the organisms inoculated into the test sample is reported in TABLE 8 for the first inoculation and TABLE 9 for the second inoculation performed after 4 weeks.

TABLE 8

(first inoculation)

|  | Contact time | 0 h | 24 h | 48 h | 1 week | 2 weeks | 3 weeks | 4 weeks |
|---|---|---|---|---|---|---|---|---|
| Bacteria | S1 Staphylococcus aureus | $10^6$ | $2.44 \times 10^3$ | 630 | <10 | <10 | <10 | <10 |
|  | S2 Pseudomonas aeruginosa, Burkholderia cepacia | $10^6$ | <10 | <10 | <10 | <10 | <10 | <10 |
|  | S3 Klebsiella pneumoniae, Enterobacter gergoviae | $10^6$ | <10 | <10 | <10 | <10 | <10 | <10 |

TABLE 8-continued (first inoculation)

| | Contact time | 0 h | 24 h | 48 h | 1 week | 2 weeks | 3 weeks | 4 weeks |
|---|---|---|---|---|---|---|---|---|
| Fungi | S4 *Candida albicans* | $10^5$ | $10^4$ | 440 | <10 | <10 | <10 | <10 |
| | S5 Mixed Moulds | $10^5$ | $10^5$ | $10^5$ | <10 | <10 | <10 | <10 |

TABLE 9

(second inoculation)

| | Contact time | 0 h | 24 h | 48 h | 1 week | 2 weeks | 3 weeks | 4 weeks |
|---|---|---|---|---|---|---|---|---|
| Bacteria | S1 *Staphylococcus aureus* | $10^6$ | $1.35 \times 10^3$ | 260 | <10 | <10 | <10 | <10 |
| | S2 *Pseudomonas aeruginosa, Burkhokleria cepacia* | $10^6$ | <10 | <10 | <10 | <10 | <10 | <10 |
| | S3 *Klebsiella pneumoniae, Enterobacter gergoviae* | $10^6$ | <10 | <10 | <10 | <10 | <10 | <10 |
| Fungi | S4 *Candida albicans* | $10^5$ | $10^4$ | $10^4$ | <10 | <10 | <10 | <10 |
| | S5 Mixed Moulds | $10^5$ | $10^4$ | 400 | <10 | <10 | <10 | <10 |

Test Sample E

A lotion base having pH of 6 having a 2% add-on of the Sample #5 was formed. The results for each of the organisms inoculated into the test sample is reported in TABLE 10 for the first inoculation and TABLE 11 for the second inoculation performed after 4 weeks.

TABLE 10

(first inoculation)

| | Contact time | 0 h | 24 h | 48 h | 1 week | 2 weeks | 3 weeks | 4 weeks |
|---|---|---|---|---|---|---|---|---|
| Bacteria | S1 *Staphylococcus aureus* | $10^6$ | 20 | <10 | <10 | <10 | <10 | <10 |
| | S2 *Pseudomonas aeruginosa, Burkholderia cepacia* | $10^6$ | <10 | <10 | <10 | <10 | <10 | <10 |
| | S3 *Klebsiella pneumoniae, Enterobacter gergoviae* | $10^6$ | <10 | <10 | <10 | <10 | <10 | <10 |
| Fungi | S4 *Candida albicans* | $10^5$ | $10^4$ | 110 | <10 | <10 | <10 | <10 |
| | S5 Mixed Moulds | $10^5$ | $10^5$ | $10^4$ | <10 | <10 | <10 | <10 |

TABLE 11

(second inoculation)

| | Contact time | 0 h | 24 h | 48 h | 1 week | 2 weeks | 3 weeks | 4 weeks |
|---|---|---|---|---|---|---|---|---|
| Bacteria | S1 Staphylococcus aureus | $10^6$ | 40 | <10 | <10 | <10 | <10 | <10 |
| | S2 Pseudomonas aeruginosa, Burkholderia cepacia | $10^6$ | <10 | <10 | <10 | 10 | 10 | <10 |
| | S3 Klebsiella pneumoniae, Enterobacter gergoviae | $10^6$ | <10 | <10 | <10 | <10 | <10 | <10 |
| Fungi | S4 Candida albicans | $10^5$ | $1.6 \times 10^3$ | $1 \times 10^3$ | <10 | <10 | <10 | <10 |
| | S5 Mixed Moulds | $10^5$ | $10^4$ | 350 | <10 | <10 | <10 | <10 |

Test Sample F

A lotion base having pH of 6 having a 2% add-on of the Sample #6 was formed. The results for each of the organisms inoculated into the test sample is reported in TABLE 12 for the first inoculation and TABLE 13 for the second inoculation performed after 4 weeks.

TABLE 12

(first inoculation)

| | Contact time | 0 h | 24 h | 48 h | 1 week | 2 weeks | 3 weeks | 4 weeks |
|---|---|---|---|---|---|---|---|---|
| Bacteria | S1 Staphylococcus aureus | $10^6$ | 130 | <10 | <10 | <10 | <10 | <10 |
| | S2 Pseudomonas aeruginosa, Burkholderia cepacia | $10^6$ | $10^3$ | <10 | <10 | <10 | <10 | <10 |
| | S3 Klebsiella pneumoniae, Enterobacter gergoviae | $10^6$ | <10 | <10 | <10 | <10 | <10 | <10 |
| Fungi | S4 Candida albicans | $10^5$ | $10^4$ | 490 | <10 | <10 | <10 | <10 |
| | S5 Mixed Moulds | $10^5$ | $10^5$ | $10^4$ | <10 | <10 | <10 | <10 |

TABLE 13

(second inoculation)

| | Contact time | 0 h | 24 h | 48 h | 1 week | 2 weeks | 3 weeks | 4 weeks |
|---|---|---|---|---|---|---|---|---|
| Bacteria | S1 Staphylococcus aureus | $10^6$ | $1.89 \times 10^3$ | 90 | <10 | <10 | <10 | <10 |
| | S2 Pseudomonas aeruginosa, Burkholderia cepacia | $10^6$ | $10^4$ | <10 | <10 | <10 | <10 | <10 |
| | S3 Klebsiella pneumoniae, | $10^6$ | <10 | <10 | <10 | <10 | <10 | <10 |

TABLE 13-continued (second inoculation)

| | Contact time | 0 h | 24 h | 48 h | 1 week | 2 weeks | 3 weeks | 4 weeks |
|---|---|---|---|---|---|---|---|---|
| Fungi | Enterobacter gergoviae S4 | $10^5$ | $10^4$ | 700 | <10 | <10 | <10 | <10 |
| | Candida albicans S5 | $10^5$ | $10^6$ | 450 | 60 | <10 | <10 | <10 |
| | Mixed Moulds | | | | | | | |

Comparative Test Sample 1C

A lotion base having pH of 6.0 having no add-on of the preservative composition is tested for comparison purposes. The results for each of the organisms inoculated into the test sample is reported in TABLE 14 for the first inoculation and TABLE 15 for the second inoculation performed after 4 weeks.

TABLE 14

(first inoculation)

| | Contact time | 0 h | 24 h | 48 h | 1 week | 2 weeks | 3 weeks | 4 weeks |
|---|---|---|---|---|---|---|---|---|
| Bacteria | S1 Staphylococcus aureus | $10^6$ | $10^6$ | $10^6$ | $10^6$ | $10^6$ | $10^6$ | $10^6$ |
| | S2 Pseudomonas aeruginosa, Burkholderia cepacia | $10^6$ | $10^6$ | $10^6$ | $10^6$ | $10^6$ | $10^6$ | $10^6$ |
| | S3 Klebsiella pneumoniae, Enterobacter gergoviae | $10^6$ | $10^6$ | $10^6$ | $10^6$ | $10^6$ | $10^6$ | $10^6$ |
| Fungi | S4 Candida albicans | $10^5$ | $10^5$ | $10^5$ | $10^5$ | $10^5$ | $10^5$ | $10^5$ |
| | S5 Mixed Moulds | $10^5$ | $10^5$ | $10^5$ | $10^5$ | $10^5$ | $10^5$ | $10^5$ |

TABLE 15

(second inoculation)

| | Contact time | 0 h | 24 h | 48 h | 1 week | 2 weeks | 3 weeks | 4 weeks |
|---|---|---|---|---|---|---|---|---|
| Bacteria | S1 Staphylococcus aureus | $10^6$ | $10^6$ | $10^6$ | $10^6$ | $10^6$ | $10^6$ | $10^6$ |
| | S2 Pseudomonas aeruginosa, Burkholderia cepacia | $10^6$ | $10^6$ | $10^6$ | $10^6$ | $10^6$ | $10^6$ | $10^6$ |
| | S3 Klebsiella pneumoniae, Enterobacter gergoviae | $10^6$ | $10^6$ | $10^6$ | $10^6$ | $10^6$ | $10^6$ | $10^6$ |
| Fungi | S4 Candida albicans | $10^5$ | $10^5$ | $10^5$ | $10^5$ | $10^5$ | $10^5$ | $10^5$ |
| | S5 Mixed Moulds | $10^5$ | $10^5$ | $10^5$ | $10^5$ | $10^5$ | $10^5$ | $10^5$ |

As can be clearly seen from the above Test Samples A-F and comparative Sample 1C, the composition is effective as a preservative composition. While the invention has been described above with references to specific embodiments thereof, it is apparent that many changes, modifications and variations can be made without departing from the invention concept disclosed herein. Accordingly, it is intended to

What is claimed is:

1. A fluid preservative composition comprising:
   (i) about 3 to about 15% by weight of an organic acid;
   (ii) about 3 to about 15% by weight of a $C_8$-$C_{18}$ fatty alcohol, the fatty alcohol comprising capryl alcohol, nanoyl alcohol, decyl alcohol, undecyl alcohol, lauryl alcohol, tridecyl alcohol, myristyl alcohol, pentadecyl alcohol, palmityl alcohol, margaryl alcohol, stearyl alcohol, or mixtures thereof;
   (iii) about 30 to about 60% by weight of an aromatic alcohol;
   (iv) about 30 to about 60% by weight of an organic solvent, wherein the organic solvent is a diol compound; and
   (v) a solubilizer, the solubilizer comprising a glycerin compound;
   wherein the solvent is free of propanediols.

2. The preservative composition according to claim 1, wherein the organic acid is sorbic acid.

3. The preservative composition according to claim 1, wherein the diol compound is selected from the group consisting of a butanediol, pentanediol, hexanediol, heptanediol, and a mixture of two or more of the diols.

4. The preservative composition according to claim 1, wherein the solvent comprises 1,3-butanediol.

5. The preservative composition according to claim 1, wherein the aromatic alcohol comprises benzyl alcohol.

6. The preservative composition according to claim 1, wherein the $C_8$-$C_{18}$ fatty alcohol comprises lauryl alcohol.

7. The preservative composition according to claim 1, wherein the $C_8$-$C_{18}$ fatty alcohol comprises myristyl alcohol.

8. The preservative composition according to claim 1, wherein the $C_8$-$C_{18}$ fatty alcohol comprises a mixture of lauryl alcohol and myristyl alcohol.

9. The preservative composition according to claim 1, wherein the preservation composition includes a stabilizer, wherein the stabilizer comprises tocopherol or gluconolactone.

10. The preservative composition according to claim 9, wherein the stabilizer is tocopherol and is present in an amount of about 0.1 to about 5.0% by weight.

11. The preservative composition according to claim 1, wherein the glycerin compound is present in an amount from about 1% up to about 8%.

12. The preservative composition according to claim 1, wherein the glycerin compound comprises caprylic/capric triglycerides.

13. The preservative composition according to claim 1, wherein the composition consists essentially of:
   (i) about 4 to about 9% by weight of the organic acid;
   (ii) about 4 to about 9% by weight of the $C_8$-$C_{18}$ fatty alcohol;
   (iii) about 30 to about 45% by weight of the aromatic alcohol; and
   (iv) about 40 to about 50% by weight of the organic solvent;
   (v) about 1% to about 20% by weight of the glycerin compound; and
   (vi) at least one of a stabilizer or a dispersant
   wherein the percentages of (i)-(vi) are based on the total amount of (i)-(vi).

14. The preservative composition according to claim 1, wherein the organic acid is sorbic acid, $C_8$-$C_{18}$ fatty alcohol comprises a mixture of lauryl alcohol and myristyl alcohol; the aromatic alcohol comprises benzyl alcohol and the organic solvent comprises 1,3-butanediol.

15. The preservative composition according to claim 1, further including a trace amount of water.

16. A personal care product comprising
   (i) a base formulation and
   (ii) an effective amount of a fluid preservative composition according to claim 1 to aid in preventing a bacterial and/or fungal infection or contamination of the base formulation.

17. The personal care product according to claim 16, wherein the fluid preservative composition is present in the personal care product in an amount of about 0.1% to about 5% by weight.

18. The personal care product according to claim 16, wherein the organic acid comprises sorbic acid.

19. The personal care product according to claim 16, wherein the base formulation is a formulation for a shampoo, a hair conditioner, a hair dye, an aftershave, a shave preparation, a bath soap, a perfume, a sun care product, an indoor tanning product, a body or hand lotion, a personal cleaner, a skin care product, makeup remover, makeup, or a wet wipe formulation.

20. A preserved composition for use in a hygiene product, a health care product, an industrial product, or household cleaning products containing the preservative composition according to claim 1.

21. A method of preserving a personal care formulation in need of preservation against bacteria and fungus infection or contamination, said method comprising adding the preservative composition according to claim 1 to a base formulation, and mixing the preservative composition with the base formulation.

22. The method according to claim 21, wherein the organic acid comprises sorbic acid.

* * * * *